Oct. 21, 1952 E. S. BOERNER Plant Pat. 1,140
ROSE PLANT
Filed Oct. 8, 1951
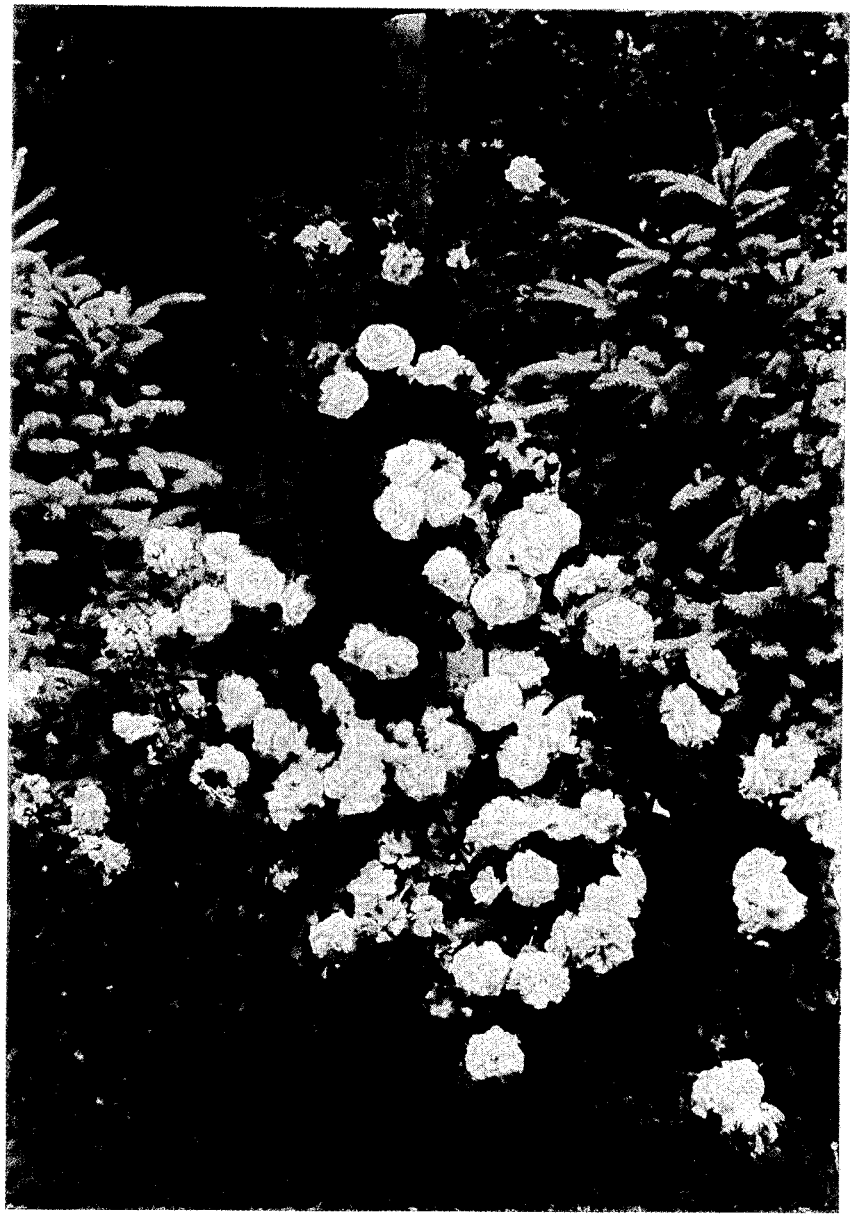
Inventor.
E. S. Boerner
By: Robbins Robb
Attorneys.

Patented Oct. 21, 1952

Plant Pat. 1,140

UNITED STATES PATENT OFFICE 1,140

ROSE PLANT

Eugene S. Boerner, Newark, N. Y., assignor to Jackson & Perkins Company, Newark, N. Y., a corporation of New York Application October 8, 1951, Serial No. 250,298

1 Claim. (Cl. 47—61)

The present invention relates to a new and distinct variety of rose plant of the climber class, originated by me by crossing the variety "New Dawn" (Plant Patent No. 1) × an unnamed and unpatented red dwarf seedling of "New Dawn."

The primary objective in making this cross was to get more color into the flowers of the very popular variety "New Dawn," while retaining the general habits of the latter. This objective was fully achieved, as evidenced by the very Deep Rose Pink color of the flowers of this new variety which has not heretofore been found in remontant climbers, by the prolific number of flowers that are produced in early spring and continuing throughout the season, and by its general and characteristic climbing growth of "New Dawn."

Asexual reproduction of the new variety by budding at Newark, New York, and at Pleasanton, California, shows that the foregoing characteristics come true to form and are established and transmitted through succeeding propagations.

The accompanying drawing shows a typical specimen plant of the new variety, with its flowers and foliage in different stages of development.

The following is a detailed description of the new variety, with color terminology in accordance with Ridgeway's Color Standards and Nomenclature:

Parentage: Seedling.

*Seed parent.*—"New Dawn."

*Pollen parent.*—An unnamed red dwarf seedling of "New Dawn."

Classification: Botanic and commercial—climber.

*Flower*

(Observations made at Newark, New York, in the fields in the mid-morning of the month of June.)

Blooming habit: Recurrent—intermittent.

Bud:

*Size.*—Medium.

*Form.*—Ovoid; is not affected by wet or hot weather.

*Color.*—When sepals first divide—Deep Rose Pink, Plate 12. When petals begin to unfurl—Thulite Pink, Plate 26. When half blown: inside of petals—Thulite Pink, Plate 26; reverse of petals—Thulite Pink, Plate 26, slightly overcast with Deep Rose Pink, Plate 12.

*Sepals.*—Slightly branched; curl back when petals begin to unfurl. Color: inside—Biscay Green, Plate 17; reverse—Light Bice Green, Plate 17.

*Calyx.* — Shape—pear. Size—small. Aspect—smooth. Odor when rubbed—none. Color—Light Bice Green, Plate 17.

*Peduncle.* — Length — medium. Aspect—rough. Color—Light Cress Green, Plate 31. Strength—erect; slender.

*Opening.*—Opens up well; is not affected by adverse weather conditions.

Bloom:

*Size.*—Medium; average size when fully expanded 3½ inches.

*Borne.*—Several together and in irregular clusters.

*Stems.*—Medium length; normal strength.

*Form.*—When first opened—cupped. Permanence—outer petals curl back.

*Petalage.*—Double (full but open center). Number of petals under normal conditions—25 to 30.

*Color.*—Center of flower—Deep Rose Pink, Plate 12. Outer petals—Thulite Pink, Plate 26. Base of petals (aiglet)—Pinard Yellow, Plate 4. Inside of petals—Thulite Pink, Plate 26, overcast with Rose Pink, Plate 12. Reverse of petals—Rose Pink, Plate 12, lightly overcast with Thulite Pink, Plate 26. General tonality from a distance—Thulite Pink, Plate 26, lightly overcast with Rose Pink, Plate 12.

*Discoloration.*—General tonality at end of first day—Thulite Pink, Plate 26, overcast with Rose Pink, Plate 12. Second day—Thulite Pink, Plate 26, overcast lightly with Rose Pink, Plate 12. Third day—Rose pink, Plate 12.

Petals:

*Texture.*—Thin; is not affected by wet or hot weather.

*Appearance.*—Inside — shiny; outside — satiny.

*Form.*—Oval.

*Arrangement.*—Imbricated (regularly arranged shinglelike). Petaloids in center—few; small.

*Persistence.*—Drop off cleanly.

*Fragrance.*—Moderate. Nature—tea (average hybrid tea scent).

*Lasting quality.*—On the plant and as cut flower—long.

Genital organs:

*Stamens, anthers.*—Medium size; many. Color—Tawny, Plate 15. Arrangement—regular around styles.

*Stamens, filaments (threads).*—Medium length. Color—Picric Yellow, Plate 4.

*Pollen.*—Color—Baryta Yellow, Plate 4.

*Styles.*—Loosely separated; uneven length; medium length; thin.
*Stigmas.*—Color—Apricot Yellow, Plate 4.
*Ovaries.*—All enclosed in calyx.

*Plant*

Form: Climber.
Growth: Vigorous; branching.
Foliage: 3 to 5 leaflets.
*Size.*—Large.
*Quantity.*—Normal abundance.
*Color.*—New foliage: upper side—Lettuce Green, Plate 5, lightly overcast with Oxblood Red, Plate 1; under side—Cosse Green, Plate 5, overcast with Oxblood Red, Plate 1.—Old foliage: upper side—Dark Cress Green, Plate 31; under side—Light Bice Green, Plate 17.
*Shape.*—Slightly pointed; round.
*Texture.*—Upper side—glossy. Under side—smooth.—Ribs and veins—ordinary.
*Edge.*—Serrated (saw toothed).
*Serration.*—Double; small.
*Leaf stem.*—Color—Light Cress Green, Plate 31.—Under side—smooth.
*Stipules.*—Long; slightly bearded.

Wood:
*New wood.*—Color—Lettuce Green, Plate 5. Bark—smooth.
*Old wood.*—Color—Spinach Green, Plate 5. Bark—smooth.
Thorns:
*Thorns.*—Quantity—on main stalks from base and on laterals from stalk—ordinary. Form—flat base; medium length; hooked downward. Color when young—Oil Green, Plate 5, tinged with Oxblood Red, Plate 1. Position—irregular.
*Prickles.*—Quantity—on main stalks and on laterals—none.
*Short needles.*—Quantity—on main stalks and on laterals—none.

I claim:

A new and distinct variety of rose plant of the climber class, substantially as herein shown and described, characterized as to novelty by the very Deep Rose Pink color of its flowers, by the prolific number of flowers produced in early spring and continuing throughout the season, and by the general similarity of its habits of growth to those of the variety "New Dawn" (Plant Patent No. 1).

EUGENE S. BOERNER.

No references cited.